United States Patent
Tanol et al.

(10) Patent No.: US 9,545,413 B2
(45) Date of Patent: *Jan. 17, 2017

(54) METHODS OF FORMING CICLOPIROX OR DERIVATIVES THEREOF IN A SUBJECT BY ADMINISTRATION OF PRODRUG

(71) Applicant: The University of Kansas, Lawrence, KS (US)

(72) Inventors: Mehmet Tanol, Jersey City, NJ (US); Scott Weir, Olathe, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/966,323

(22) Filed: Dec. 11, 2015

(65) Prior Publication Data

US 2016/0095870 A1    Apr. 7, 2016

Related U.S. Application Data

(60) Continuation-in-part of application No. 14/059,287, filed on Oct. 21, 2013, now Pat. No. 9,243,014, which is a division of application No. 13/310,087, filed on Dec. 2, 2011, now Pat. No. 8,609,637.

(60) Provisional application No. 61/419,218, filed on Dec. 2, 2010.

(51) Int. Cl.
| | |
|---|---|
| *A01N 57/00* | (2006.01) |
| *A61K 31/675* | (2006.01) |
| *C07F 9/58* | (2006.01) |
| *C07F 9/59* | (2006.01) |
| *C07F 9/09* | (2006.01) |
| *C07F 9/11* | (2006.01) |

(52) U.S. Cl.
CPC ............ *A61K 31/675* (2013.01); *C07F 9/091* (2013.01); *C07F 9/094* (2013.01); *C07F 9/11* (2013.01); *C07F 9/581* (2013.01); *C07F 9/591* (2013.01)

(58) Field of Classification Search
None
See application file for complete search history.

(56) References Cited

U.S. PATENT DOCUMENTS

| | | | |
|---|---|---|---|
| 2004/0077540 A1 | 4/2004 | Quay | |
| 2004/0198680 A1 | 10/2004 | Krieg | |
| 2006/0272103 A1 | 12/2006 | Barbarat | |

FOREIGN PATENT DOCUMENTS

WO    2010048712 A1    5/2010

OTHER PUBLICATIONS

Huttunen et al., Current Topics in Medicinal Chemistry, 2011, 11, 2265-2287.*
Testa in Biochemical Pharmacology 68, (2004) 2097-2106.*
Burger's Medicinal Chemistry and Drug Discovery (1995, 5th Edition, vol. I: Principles and Practice).*
Banker Modern Pharmaceutics (3rd Edition) 1996.*
Eberhard et al, Blood, 2009, 114, 3064-3073.*
International Search Report dated Jul. 23, 2012 as received in application No. PCT/US2011/063070.
Written Opinion of the International Searching Authority dated Jul. 23, 2012 as received in application No. PCT/US2011/063070.
Schafer et al. Drug Discovery Today, 2008, 13 (21/22), 913-916.
Horig et al. Journal of Translational Medicine 2004, 2(44), 1-8.
H. Bundgaard: "Design of Prodrugs", 1985, Elsevier.
Extended European Search Report dated Mar. 4, 2014 for Application No. 11845102.0.

* cited by examiner

*Primary Examiner* — Dennis Heyer
*Assistant Examiner* — Daniel M Podgorski
(74) *Attorney, Agent, or Firm* — Stinson Leonard Street LLP

(57) ABSTRACT

A method of forming a compound in a subject can include: providing a composition having a prodrug compound represented by a structure of Formula 1 or stereoisomer thereof or pharmaceutically acceptable salt thereof; and administering the composition to a subject such that the prodrug compound has a phosphoryloxyalkyl prodrug moiety removed therefrom to form the compound in the subject and to form the separate phosphoryloxyalkyl compound. The prodrug can be included in a pharmaceutical composition for use in treatment of fungus, various cancers (e.g., bladder, breast, etc.), dermatitis, superficial mycoses; inflammation, tinea pedis, tinea cruris, and tinea corporis, *Trichophyton rubrum, Trichophyton mentagrophytes, Epidermophyton floccosum,* and *Microsporum canis,* candidiasis (moniliasis), *Candida albicans,* tinea (pityriasis) vesicolor, *Malassezia furfur,* acute myeloid leukemia, acute lymphoid leukemia, chronic myelogenous leukemia, lymphoma or multiple myeloma.

16 Claims, 11 Drawing Sheets

Scheme 2

Scheme 3

Scheme 3A

Molecular Weight: 634.55

Scheme 4

Scheme 5

Scheme 6

Scheme 7

Scheme 8

US 9,545,413 B2

METHODS OF FORMING CICLOPIROX OR DERIVATIVES THEREOF IN A SUBJECT BY ADMINISTRATION OF PRODRUG

CROSS-REFERENCE TO RELATED APPLICATIONS

This patent application is a continuation-in-part of U.S. patent application Ser. No. 14/059,287 filed Oct. 21, 2013, which is a divisional of U.S. patent application Ser. No. 13/310,087 filed Dec. 2, 2011 now U.S. Pat. No. 8,609,637, which claims benefit of U.S. Provisional Patent Application 61/419,218 filed on Dec. 2, 2010, and which applications are incorporated herein by specific reference in their entirety.

BACKGROUND

The molecule 6-cyclohexyl-1-hydroxy-4-methylpyridin-2(1H)-one, also known as Ciclopirox, is a commercially available antifungal agent as an olamine salt. Ciclopirox olamine has been used to treat superficial mycoses and *Tinea versicolor* following topical application to the skin. Following enteral administration, ciclopirox undergoes significant first-pass effect resulting in low oral bioavailability. The oral route of administration is also associated with gastrointestinal toxicities observed in animals and humans limiting its benefit in animal and human health applications. Ciclopirox olamine has poor solubility, limiting opportunities to deliver the antifungal agent via parenteral administration of suitably potent solutions and suspensions. As such, it would be beneficial to configure ciclopirox for improved water solubility in order to deliver the drug by parenteral routes of administration.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
FIG. 1 illustrates a schematic representation of a method of preparing 6-cyclohexyl-1-hydroxy-4-methylpyridin-2(1H)-one, which is referred to herein as Cyclopirox (Scheme 1).

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to prodrugs of 6-cyclohexyl-1-hydroxy-4-methylpyridin-2(1H)-one, also known as ciclopirox. The ciclopirox prodrugs can include a phosphoryloxymethyl (POM) moiety or other phosphoryloxyalkyl (POA) moiety in order to provide improve solubility and bioavailability to ciclopirox. While the description herein describes ciclopirox-POM and the POM prodrug moiety in detail, the prodrug may be ciclopirox-POA and the prodrug moiety is POA. However, when the prodrug is described as ciclopirox-POM and the prodrug moiety as POM it should be understood that the methyl of POM may be an alkyl, substituted or unsubstituted so as to be ciclopirox-POA and POA. As such, POA is a genus that includes the POM species. Discussions of POM herein as an example refer to POA, and discussions of POA refer to the species POM.

The ciclopirox-POM of the present invention can also include derivatives of ciclopirox that include the POM prodrug moiety, which derivative prodrugs can be referred to herein generally under the term ciclopirox-POM or may be specifically referenced as ciclopirox-POM derivatives. The ciclopirox-POM prodrugs of the present invention can be prepared with traditional chemistry techniques, such as those described herein.

The ciclopirox-POM prodrug has been shown to improve the aqueous solubility of ciclopirox, and thereby can improve its bioavailability via a number of routes of administration. Accordingly, the ciclopirox-POM prodrug overcomes limitations with the formulation and/or delivery route of ciclopirox or other forms of ciclopirox, such as a ciclopirox salt like ciclopirox olamine. The improved solubility of the ciclopirox-POM prodrug can now allow for improved pharmaceutical compositions for administering effective amounts of ciclopirox. The pharmaceutical compositions can be formulated to be suitable for the route of administration, such as intravenous, subcutaneous, oral, or topical.

The ciclopirox-POM prodrug is configured so that the POM moiety is cleaved off by phosphatase enzymes in order to produce the original parent drug ciclopirox that is biologically active. As such, the ciclopirox-POM can be administered to a living subject, and then be enzymatically processed into bioactive ciclopirox within the body of the subject. While the subject usually will be human, the ciclopirox-POM prodrugs may be found to be suitable for a wide variety of animals, such as mammals, birds, reptiles, or the like.

While ciclopirox has traditionally been used as a topical antifungal, the different formulations available for the ciclopirox-POM prodrugs of the present invention may provide therapeutically effective amounts of ciclopirox for other maladies that have been shown or that may be developed to be suitable for ciclopirox treatment. Accordingly, the ciclopirox-POM prodrugs may be used in therapies for: inhibition, treatment, and/or prevention of a fungus; inhibition, treatment, and/or prevention of various types of cancer (e.g., bladder, breast and others described herein); inhibition, treatment, and/or prevention of dermatitis; inhibition, treatment, and/or prevention of superficial mycoses; for inhibition, treatment, and/or prevention of inflammation (e.g., as an anti-inflammatory, or NSAID); and inhibition, treatment, and/or prevention of one or more of tinea pedis, tinea cruris, and tinea corporis, *Trichophyton rubrum*, *Trichophyton mentagrophytes*, *Epidermophyton floccosum*, and *Microsporum canis*, candidiasis (moniliasis), *Candida albicans*, tinea (pityriasis) vesicolor, or *Malassezia furfur*. It has also been found that that ciclopirox selectively eliminates viral infection by HIV-1, which can be delivered as ciclopirox-POA prodrug (ciclopirox-phosphoryloxyalkyl prodrug).

The ciclopirox-POM prodrug improves bioavailability of ciclopirox such that increased amounts and distributions of the prodrug can be effective on cellular and subcellular levels. That is, more ciclopirox can be available throughout a subject as well as within individual cells of a subject. The increased amount of available ciclopirox improves the bioactivity and therapeutic potential, as well as improves the ability to modulate cellular processes. Accordingly, the ciclopirox-POM can be used for disrupting DNA repair, cell division, or intranuclear transport in a cell. The cells may be in vivo, ex vivo, or in vitro.

While prodrugs of ciclopirox have been described, such prodrugs have been limited to conventional esters formed with available hydroxyl and/or amino groups, such as by acylation of activated acids in the presence of a base. The esters described can include produgs that have phenyl esters, aliphatic ($C_8$-$C_{24}$) esters, acyloxymethyl esters, carbamates, and amino acid esters (see WO 2010/048712, which is incorporated herein by specific reference in its entirety).

Additionally, prodrugs with increased solubility have been created for compounds that include secondary and tertiary amine containing drugs. Examples of such prodrugs include N-phosphoryloxymethyl (POM) prodrugs where the methyl group of the POM moiety is coupled to a secondary or tertiary amine (see U.S. Pat. No. 5,985,856, which is incorporated herein by specific reference in its entirety).

It has now been found that alternative chemistry techniques can couple a POM prodrug entity or other POA prodrug entity to ciclopirox in order to form the ciclopirox-POM prodrugs or other ciclopirox-POA prodrugs of the present invention. The chemical synthesis protocols can conjugate ciclopirox, shown in below, through its hydroxyl group rather than through a secondary or tertiary amine. While ciclopirox does include a cyclic nitrogen, it has been found that such a nitrogen is undesirable to be linked to a POA due to the hydroxyl group or oxygen linked to the nitrogen possibly being important for the biological activity of ciclopirox. As such, the present invention provides chemistry techniques to conjugate a POA moiety to the hydroxyl group that is linked to the ring nitrogen of ciclopirox.

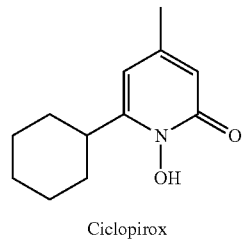

Ciclopirox

In one embodiment, the present invention includes a prodrug of ciclopirox or its derivatives. The prodrug can include a structure of Formula 1 or derivative thereof or stereoisomer thereof as well as a pharmaceutically acceptable salt thereof.

Formula 1

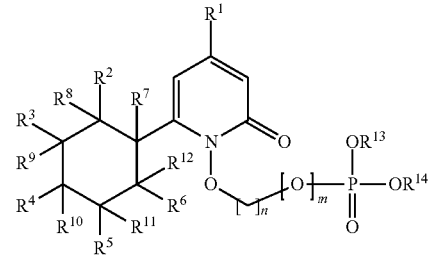

In the formulae, $R^1$-$R^5$ each independently can include a hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, derivatives thereof, substituted or unsubstituted, or combinations thereof as well as other well-known chemical substituents. $R^{13}$ and/or $R^{14}$ can be a positive ion such as a sodium ion, such that the compound forms a salt. Also, $R^{13}$ and/or $R^{14}$ independently can include a positive ion to form a salt with the prodrug or one or more of hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, or combinations thereof. The methyl linker can be expanded to a larger aliphatic group that is substituted or unsubstituted if desired or the methyl may be omitted, such that n can be about 0-20 or 1-20, more preferably 1-10, and most preferably 1-4. The linker may also have one or two oxygen atoms, such that m can be 0, 1 or 2. When n is 1, the prodrug moiety is a POM. When n is 2-20, the prodrug moiety is POA. Often, m is 1.

In one embodiment, $R^{13}$ and/or $R^{14}$ may independently be any one of various positive ions. In one example, $R^{13}$ and/or $R^{14}$ can independently include ions with positive charge of +1, such as lithium, sodium, potassium, rubidium, cesium, or francium or other complex ion. The $R^{13}$ and/or $R^{14}$ can be an alkali metal. Also, the $R^{13}$ and/or $R^{14}$ can independently be a group 1 ion, such as a sodium ion or potassium ion. Accordingly, the bond between the oxygen and $R^{13}$ and/or $R^{14}$ can be covalent or ionic.

In one embodiment, the $R^{13}$ and/or $R^{14}$ can independently be a protecting group. Examples of protecting groups can include tert-butyl and benzyl; however, other organic-based protecting groups can be used. These protecting groups may be left on the prodrug for administration, or removed prior to administration. The $R^{13}$ and/or $R^{14}$ may be any substituent, such as those recited for $R^1$ to $R^{12}$.

In one embodiment, $R^1$ is a short aliphatic, such as a methyl or other alkyl.

In one embodiment, the $R^2$-$R^{12}$ are all hydrogen.

In one embodiment, the $R^{13}$ and/or $R^{14}$ are each independently a hydrogen or ion.

In one embodiment, the $R^{13}$ and/or $R^{14}$ are each independently a benzyl or tert-butyl or other substituent.

In one embodiment, the $R^{13}$ or $R^{14}$ includes a ciclopirox-POM or other ciclopirox-POA and the other is hydrogen, which is shown in Formula 10 below.

In one embodiment, the present invention can include compounds with a structure of Formula 2 or derivative thereof or stereoisomer thereof. The n, m, $R^1$, and $R^{13}$ and/or $R^{14}$ can be the same as recited above for Formula 1.

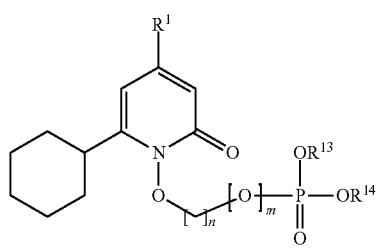

Formula 2

In one embodiment, the compounds can include the structure of Formula 3 or derivative thereof or stereoisomer thereof. The n, m, $R^1$, and $R^{13}$ and/or $R^{14}$ can be the same as recited above for Formula 1.

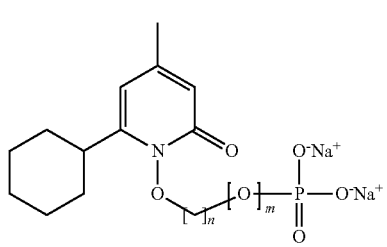

Formula 3

In one embodiment, the compounds can include the structure of Formula 4 or derivative thereof or stereoisomer thereof. The n and m can be the same as recited above for Formula 1.

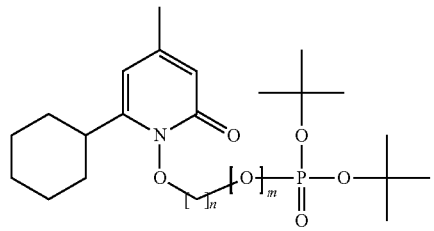

Formula 4

In one embodiment, the compounds can include the structure of Formula 5 or derivative thereof or stereoisomer thereof. The n and m can be the same as recited above for Formula 1.

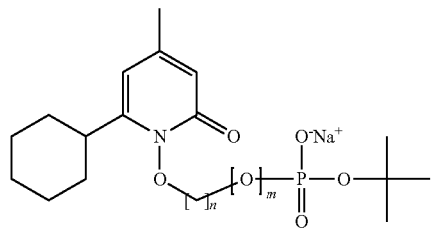

Formula 5

In one embodiment, the compounds can include the structure of Formula 6 or derivative thereof or stereoisomer thereof. The n and m can be the same as recited above for Formula 1.

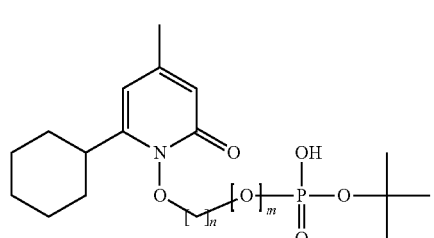

Formula 6

In one embodiment, the compounds can include the structure of Formula 7 or derivative thereof or stereoisomer thereof. The n and m can be the same as recited above for Formula 1.

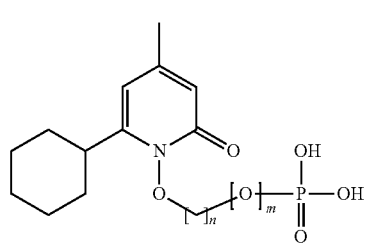

Formula 7

In one embodiment, the compounds can include the structure of Formula 8 or derivative thereof or stereoisomer thereof. The n and m can be the same as recited above for Formula 1.

Formula 8

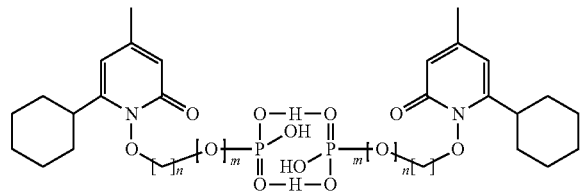

In one embodiment, the compounds can include the structure of Formula 9 or derivative thereof or stereoisomer thereof. The n and m can be the same as recited above for Formula 1.

Formula 9

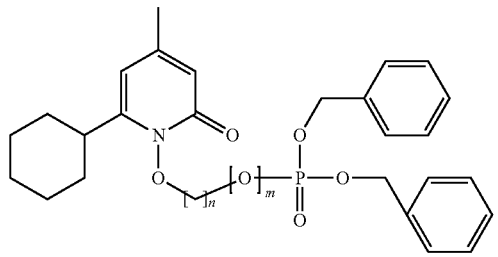

In one embodiment, the compounds can include the structure of Formula 10 or derivative thereof or stereoisomer thereof.

Formula 10

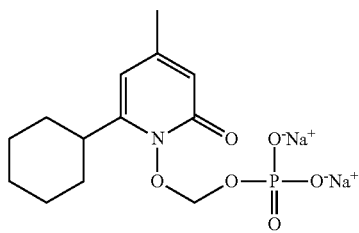

Any of the compounds may be prepared as pharmaceutically acceptable salts, if possible. Any common pharmaceutically acceptable salt ion can be used.

Additionally, any of the compounds described herein and represented by the chemical formulae can have any of the R groups ($R^1$-$R^{14}$) independently selected from substituents selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—$N^+$≡$C^-$), cyanato (—O—C≡N), isocyanato (—O—$N^+$≡$C^-$), isothiocyanato (—S—C≡N), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$S_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)(O—)), phospho (—$PO_2$), phosphino (—$PH_2$), derivatives thereof, and combinations thereof.

The POM prodrug moiety of a prodrug compound can be cleaved off by any mechanism, such as hydrolysis or enzymatically to result in the POM compound and a biologically active compound. Thus, a method of forming a biologically active compound in a subject can include administering the prodrug compound.

Any POA prodrug moiety of a prodrug compound can be cleaved off by any mechanism, such as hydrolysis or enzymatically to result in the POA compound and a biologically active compound. Thus, a method of forming a biologically active compound in a subject can include administering the prodrug compound.

Pharmaceutical Compositions

In one embodiment, the ciclopirox-POM prodrug or other ciclopirox-POA prodrug can be included in a pharmaceutical composition. The pharmaceutical compositions can be formulated to be suitable for the route of administration, such as intravenous, subcutaneous, oral, or topical.

In one embodiment, a pharmaceutical composition can include the ciclopirox-POM prodrug as described herein. For example, the pharmaceutical composition can include a pharmaceutically acceptable carrier. Since the ciclopirox-POA prodrug is now highly water soluble, the pharmaceutically acceptable can include water. However, the carrier can be sufficient in order to administer the ciclopirox-POA prodrug so that it reaches the aqueous environment of a subject to which it is administered, such as a human of the cells thereof.

In one embodiment, the pharmaceutical composition can include the ciclopirox-POM prodrug being present in an amount greater than about 0.77%, more preferably greater than about 1%; or most preferably greater than about 2%.

In one embodiment, the pharmaceutical composition can include water as a carrier.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences. On this basis, the compositions include, albeit not exclusively, solutions of the substances in association with one or more pharmaceutically acceptable vehicles or diluents, and contained in buffered solutions with a suitable pH and iso-osmotic with the physiological fluids.

In one embodiment, the effective amount of ciclopirox-POA prodrug is within the range of about 1 to about 200 mg/kg body weight of a subject. In one aspect, the effective amount of ciclopirox-POA prodrug is within the range of about 5 to about 50 mg/kg body weight. The ciclopirox-POA prodrug can be prepared into a solid dosage form that contains from about 20 mg to about 1000 mg of ciclopirox-POA prodrug. In one aspect, the composition can include about 20 mg to about 200 mg of ciclopirox-POA prodrug/kg body weight of subject, and can be formulated into a solid oral dosage form, a liquid dosage form, or an injectable dosage. However, other amounts can be used. For example, the drug can be administered over a wide range of doses, such as 0.5 mg/m$^2$ to 300 mg/m$^2$, 1 mg/m$^2$ to 200 mg/m$^2$, 5 mg/m$^2$ to 150 mg/m$^2$, 10 mg/m$^2$ to 75 mg/m$^2$, or any suitable amount.

In one embodiment, the present invention can include a pharmaceutical composition configured for treatment of a leukemic disorder. Such a composition can include an effective amount of ciclopirox-POA prodrug that can be administered orally or intravenous or other injection.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (e.g., Tween®), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesyl-phosphotidyl-ethanolamine (DOPE), and liposomes. Such compositions should contain a therapeutically effective amount of the compound, together with a suitable amount of carrier so as to provide the form for direct administration to the patient.

The compositions described herein can be administered for example, by parenteral routes of administration such as intravenous, subcutaneous, intramuscular, intracranial, intraorbital, ophthalmic, intraventricular, intracapsular, intraspinal, intracisternal, intraperitoneal, intranasal, aerosol or oral administration. Common carriers or excipients can be used for preparing pharmaceutical compositions designed for such routes of administration.

Another aspect provides a commercial package comprising a composition described herein, and associated therewith instructions for the use thereof for treatment of a disorder for which ciclopirox is effective, such as those described herein.

For example, the package can include a suitable amount for treating a leukemic disorder, such as acute myeloid leukemia or acute lymphoid leukemia, in a subject in need of such treatment. In another embodiment, the commercial package can include instructions for administration and/or a therapeutic regimen for the treatment of chronic myelogenous leukemia, lymphoma or multiple myeloma. Another embodiment provides a commercial package comprising a composition described herein, and associated therewith instructions for the inducing cell death and/or inhibiting surviving activity or level in a leukemic disorder cell such as a leukemia cell.

In one embodiment, the composition is devoid of an olamine. In fact, the prodrug can be devoid of an olamine. Accordingly, the composition can be devoid of a ciclopirox olamine or derivative thereof.

In one embodiment, the prodrug can be present in a therapeutically effective amount for use as a therapy. For example, the therapeutically effective amount can be sufficient for one or more of the following: for use in treatment of a fungus; for use in treatment of cancer; for use in treatment of dermatitis; for disrupting DNA repair, cell division, or intranuclear transport in a cell; for use in treatment of superficial mycoses; for use as an anti-inflammatory; for use in treatment of one or more of tinea pedis, tinea cruris, and tinea corporis, *Trichophyton rubrum, Trichophyton mentagrophytes, Epidermophyton floccosum*, and *Microsporum canis*, candidiasis (moniliasis), *Candida albicans*, tinea (pityriasis) vesicolor, or *Malassezia furfur*; for use in treating acute myeloid leukemia or acute lymphoid leukemia; chronic myelogenous leukemia, lymphoma or multiple myeloma, or others.

In one embodiment, a method of forming a compound in a subject can include: providing a composition having a prodrug compound represented by a structure of Formula 1 or stereoisomer thereof or pharmaceutically acceptable salt thereof; and administering the composition to a subject such that the prodrug compound has a phosphoryloxymethyl prodrug moiety removed therefrom to form the compound in the subject. Formula 1 is the same as provided herein. The R groups e.g., $R^1$-$R^{15}$, can be as described herein or independently any one or more of the substituents selected from the group of hydrogen, $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_6$-$C_{20}$ aryloxy, acyl (including $C_2$-$C_{24}$ alkylcarbonyl (—CO-alkyl) and $C_7$-$C_{20}$ arylcarbonyl (—CO-aryl)), acyloxy (—O-acyl), $C_2$-$C_{24}$ alkoxycarbonyl (—(CO)—O-alkyl), $C_7$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_7$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), di-substituted arylcarbamoyl (—(CO)—NH-aryl)$_2$, thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-substituted arylthiocarbamoyl (—(CS)—NH-aryl), di-substituted arylthiocarbamoyl (—(CS)—NH-aryl)$_2$, carbamido (—NH—(CO)—NH$_2$,), mono-($C_1$-$C_{24}$ alkyl)-substituted carbamido (—NH—(CO)—NH($C_1$-$C_{24}$ alkyl)), di-($C_1$-$C_{24}$ alkyl)-substituted carbamido (—NH—(CO)—N($C_1$-$C_{24}$ alkyl)$_2$), mono-substituted aryl carbamido (—NH—(CO)—NH-aryl), di-substituted aryl carbamido (—NH—(CO)—N-(aryl)$_2$) cyano(—C≡N), isocyano (—N$^+$≡C$^-$), cyanato (—O—C≡N), isocyanato (—O—N$^+$≡C$^-$), thiocyanato (—S—C≡N), isothiocyanato (—S—N$^+$≡C$^-$), azido (—N=N$^+$=N$^-$), formyl (—(CO)—H), thioformyl (—(CS)—H), amino (—NH$_2$), mono- and di-(C$_1$-C$_{24}$ alkyl)-substituted amino, mono- and di-(C$_6$-C$_{20}$ aryl)-substituted amino, C$_2$-C$_{24}$ alkylamido (—NH—(CO)-alkyl), C$_6$-C$_{20}$ arylamido (—NH—(CO)-aryl), imino (—CR=NH where R is hydrogen, C$_1$-C$_{24}$ alkyl, C$_6$-C$_{20}$ aryl, C$_7$-C$_{24}$ alkaryl, C$_7$-C$_{24}$ aralkyl, etc.), alkylimino (—CR=N(alkyl), where R=hydrogen, C$_1$-C$_{24}$ alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfonic acid (—SO$_2$—OH), sulfonato (—SO$_2$—O$^-$), C$_1$-C$_{24}$ alkylsulfanyl (—S-alkyl; also termed "alkylthio"), C$_6$-C$_{20}$ arylsulfanyl (—S-aryl; also termed "arylthio"), C$_1$-C$_{24}$ alkylsulfinyl (—(SO)-alkyl), C$_6$-C$_{20}$ arylsulfinyl (—(SO)-aryl), C$_1$-C$_{24}$ alkylsulfonyl (—SO$_2$-alkyl), C$_6$-C$_{20}$ arylsulfonyl (—SO$_2$-aryl), phosphono (—P(O)(OH)$_2$), phosphonato (—P(O)(O$^-$)$_2$), phosphinato (—P(O)(O—)), phospho (—PO$_2$), phosphino (—PH$_2$), any with or without hetero atoms (e.g., N, O, P, S, or other) where the hetero atoms can be substituted (e.g., hetero atom substituted for carbon in chain or ring) for the carbons or in addition thereto (e.g., hetero atom added to carbon chain or ring) swapped, derivatives thereof, and combinations thereof.

In one embodiment, the prodrug moiety is cleaved from the prodrug compound. Such a prodrug moiety can be a phosphoryloxymethyl prodrug moiety, such as having a structure of Formula 11:

Formula 11

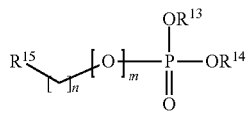

wherein: $R^{15}$ includes one or more of a positive ion, sodium ion, hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, substituted or unsubstituted, or combinations thereof. In one example, $R^{15}$ results from enzymatic cleavage of the prodrug compound. In one example, $R^{15}$ is hydrogen. It is thought that it is possible in the subject that the POA or POM may conjugate with other substances when cleaved from the ciclopirox or derivative thereof, which may form a wide variety of POA compounds or form POM. In one aspect, the phosphoryloxyalkyl prodrug moiety has a structure of Formula 11A. In one aspect, the phosphoryloxymethyl prodrug moiety has a structure of Formula 11B.

Formula 11A

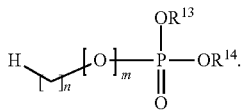

Formula 11B

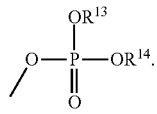

In one embodiment, $R^{15}$ includes one or more of hydrogen, halogen, hydroxyls, alkoxys, straight aliphatics, branched aliphatics, cyclic aliphatics, substituted aliphatics, unsubstituted aliphatics, saturated aliphatics, unsaturated aliphatics, amines, primary amines, secondary amines, tertiary amines, aliphatic amines, carbonyls, carboxyls, amides, esters, amino acids, peptides, polypeptides, substituted or unsubstituted, or combinations thereof.

In one embodiment, $R^{15}$ includes one or more of hydrogen, halogen, hydroxyls, alkoxys, straight aliphatics, branched aliphatics, cyclic aliphatics, substituted aliphatics, unsubstituted aliphatics, saturated aliphatics, unsaturated aliphatics, amino acids, peptides, polypeptides, substituted or unsubstituted, or combinations thereof.

In one embodiment, $R^{15}$ includes one or more of hydrogen, halogen, hydroxyls, alkoxys, straight aliphatics, branched aliphatics, cyclic aliphatics, substituted aliphatics, unsubstituted aliphatics, saturated aliphatics, unsaturated aliphatics, or combinations thereof.

In one embodiment, the active compound resulting from the prodrug compound can be any of the compounds described herein, such as the ciclopirox compounds, such as derivatives of Formulae 2-10 that lack the prodrug moiety. It should be noted that the ions for the POA or POM can be any appropriate cation or combinations of cations, such as any monovalent cation, such as sodium or potassium, and possibly lithium or the like. In one embodiment, the active compound that results from the prodrug compound can have a structure of Formula 12.

Formula 12

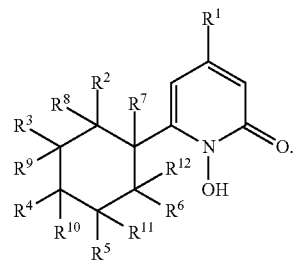

For Formula 12, the R groups (e.g., $R^1$-$R^{12}$) can be as defined herein. In one example, $R^1$ is an alkyl (e.g., methyl) and $R^2$-$R^{12}$ are hydrogen, such as ciclopirox.

In one embodiment, the phosphoryloxymethyl prodrug moiety is enzymatically cleaved from the prodrug compound so as to form the compound.

In one embodiment, the phosphoryloxyalkyl prodrug moiety is enzymatically cleaved from the prodrug compound so as to form the compound.

In one embodiment, the compound is formed in an amount sufficient for disrupting DNA repair in a cell in the subject.

In one embodiment, the compound is formed in an amount sufficient for disrupting cell division in the subject.

In one embodiment, the compound is formed in an amount sufficient for disrupting intranuclear transport in a cell in the subject.

The prodrug compound can be used to treat different cancers, such as bladder cancer. The treatment of bladder cancer with the prodrug compound is described in PCT/US2015/0059955 filed Nov. 10, 2015, which is incorporated herein by specific reference in its entirety. The experimental section, figures, tables and all other data of PCT/US2015/0059955 is specifically incorporated as it shows the prodrug compound is cleaved into the active compound and the POA (e.g., (POM) compound. Also, U.S. Provisional Patent Application 62/134,747 filed Mar. 18, 2015 and U.S. Provisional Patent Application 62/078,069 filed Nov. 11, 2014 are incorporated herein by specific reference in their entireties.

It has now been found that the compounds of the present invention are useful for treating bladder cancer. The bladder cancer can include NMIBC (non-muscle invasive bladder cancer) and MIBC (Muscle invasive bladder cancer), as well as other bladder cancers. Giving the prodrug by systemic injection (e.g., intravenous, intramuscular, subcutaneous, etc.) results in active, clinically relevant concentrations (e.g., significant concentrations) of the active agent ciclopirox being selectively delivered to the entire urinary tract. This can treat non-muscle invasive or superficial bladder cancer.

The prodrug converts to the active ciclopirox compound that effectively suppresses stem cells in bladder cancer and specifically targets the Notch-1 signaling pathway. It has been demonstrated that in the presence of the compound, signaling is significantly suppressed and the compound is affecting bladder cancer through this mechanism. Suppressing Notch is a significant activity for the compound to inhibit bladder and other cancers where Notch signaling is active (e.g. colon cancer, osteosarcoma).

NMIBC starts out by a cancer of the outer lining (urothelium) of the urinary tract (e.g., the lining that's up against the urine), and the cancer cells that are on the outer lining start invading inwardly into the muscle of the bladder, and then the cancer spreads throughout the body. However, the activity of ciclopirox and the delivery as the prodrug allows the drug to inhibit a pathway that is associated with the invasiveness of this particular cancer.

In one embodiment, the prodrug can be administered to provide the anticancer activity of ciclopirox to treat leukemia, lymphoma, colorectal cancer, hepatoma, rhabdomyosarcoma, and breast cancer cell lines, as well as others, such as but not limited to pancreatic cancer, renal cell carcinoma, hematologic malignancies, cervical cancer, myeloma, and possibly others.

Accordingly, the ciclopirox-POA can be used against a broad spectrum of cancer lines by disrupting DNA repair, cell division, or intranuclear transport in a cell, by inhibiting Notch signaling, and inhibiting any other biological pathway described herein.

The ciclopirox-POM prodrug, based on activity of ciclopirox, may also be used to induce autophagy, inhibit mTOR, downregulate cyclins A, B 1, D1 and E as well as CDK2 and CDK4, and other activities.

The methods of treating bladder cancer with the prodrug can include administering ciclopirox-POM prodrug (e.g., prodrug) systemically for the treatment of bladder cancer, which provides surprising and unexpected results, such as described herein.

It has been found that systemic administration of ciclopirox-POM prodrug results in the selective delivery of clinically significant concentrations of the active, anticancer agent, ciclopirox (free acid) to the entire urinary tract.

Current treatment of non-muscle invasive bladder cancer (NMIBC, formerly referred to as superficial bladder cancer) is via bladder instillation. There are no current drug therapies for NMIBC administered by any route other than bladder instillation. Bladder instillation of anticancer agents only exposes bladder cancer to anticancer agents for the period of time patients are able to retain fluids in their bladders (e.g., two hours). Secondly, bladder instillation does not deliver drug to the entire urinary tract, i.e., the ureters, collecting system, and kidneys that anatomically sits above the bladder. Up to 10% of NMIBC patients have upper urinary tract disease. Contrary thereto, the present invention includes systemic delivery (e.g., injection) that provides active drug to the entire urinary tract. However, the therapeutics may also be delivered by bladder installation.

Bladder cancer presents as two diseases, NMIBC and muscle invasive bladder cancer (MIBC). Approximately three-fourths of newly diagnosed bladder cancer patients present with NMIBC. NMIBC, as it invades into bladder muscle, becomes MIBC. MIBC often metastasizes, requiring systemically administered chemotherapy agents. It has now been surprising and unexpectedly demonstrated that ciclopirox possesses anticancer activity in NMIBC and MIBC bladder cancers, and systemic delivery of ciclopirox-POM prodrug provides the ciclopirox to these bladder cancer cells. The ciclopirox from ciclopirox-POM prodrug delivery inhibits cell proliferation, colony formation, and spheroid formation in well characterized NMIBC and MIBC cell lines. Although that ciclopirox's fungicidal activity is mediated through its ability to chelate iron, and interrupt iron-dependent intracellular processes, ciclopirox in vitro anti-cancer activity in independent of commercially available iron chelators. For the first time, it was demonstrated that ciclopirox inhibits the Notch-1 signaling pathway, which is a pathway recently identified as being overexpressed in invasive bladder cancer, and a pathway that is overexpressed in cancer stem cells across a number of cancers. Accordingly, ciclopirox-POM prodrug can be used in treatment of all forms of bladder cancer, and in cancer stem cells of many different cancers where the Notch signaling pathway is active.

The improved solubility of the ciclopirox-POA prodrug can now allow for improved pharmaceutical compositions for administering effective amounts of ciclopirox by injection. The pharmaceutical compositions can be formulated to be suitable for injectable routes of administration, such as intravenous, subcutaneous, and intramuscular.

Synthesis

Generally, ciclopirox can be obtained and then reacted through the reaction protocols described herein in order to produce the ciclopirox-POM prodrug. Also, a ciclopirox derivative can be obtained and reacted following the synthetic protocols described herein, where a ciclopirox derivative reagent will result in a corresponding ciclopirox-POM derivative prodrug. In some instances, the ciclopirox or derivative thereof can be obtained in a salt, such as an olamine salt. Accordingly, the reaction scheme can include desalting the ciclopirox prior to conjugation with the POM prodrug moiety. However, the reagents can substitute an alkyl for the methyl so that the POA prodrug moiety can be conjugated to ciclopirox.

In the figures and associated following descriptions of chemical reactions and the corresponding reactants, abbreviations are used to describe chemicals, which abbreviations are defined as follows: EDAC is N-(3-Dimethylaminopropyl)-N'-ethylcarbodiimide hydrochloride; DIAD is diisopropyl azodicarboxylate; BBDI is 1-tert-Butoxy-2-tert-butoxycarbonyl-1,2-dihydroisoquinoline; DICD is diisopropyl carbodiimide; and DBP is dibenzyl phosphate.

In one embodiment, the present invention provides a method of preparing 6-cyclohexyl-1-hydroxy-4-methylpyridin-2(1H)-one, which method can include reaction Scheme 1 as shown in FIG. 1. The reaction of Scheme 1 prepares a ciclopirox from an olamine salt thereof. Briefly, ciclopirox olamine (5 g, 18.6 mmol) can be dissolved in 2 N HCl, extracted with EtOAc, and precipitated with hexane in order to obtain ciclopirox (about an 84% yield).

Figure 2:
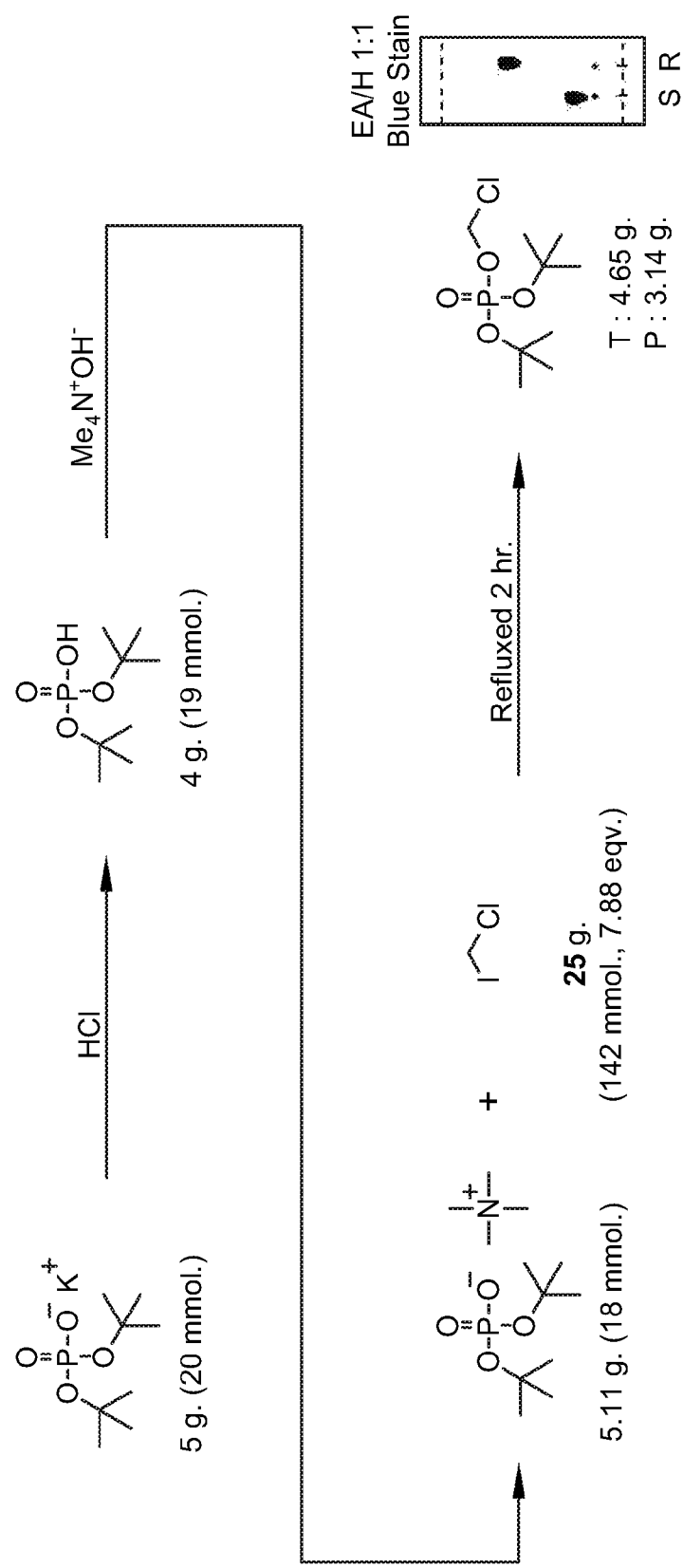
FIG. 2 illustrates a schematic representation of a method of preparing di-tert-butyl(chloromethyl)phosphate (Scheme 2).

In one embodiment, the present invention provides a method of preparing a reagent for use in preparing a prodrug of 6-cyclohexyl-1-hydroxy-4-methylpyridin-2(1H)-one, which method can include reaction Scheme 2 as shown in FIG. 2. The reaction Scheme 2 provides a reagent for preparation of a reagent of the POM prodrug moiety, which is di-tert-butyl(chloromethyl)phosphate. Briefly, potassium di-tert phosphate (5 g, 20 mmol) is dissolved in a minimum amount of cold water and 6 N HCl is added drop-wise in order to form a precipitate, and then the precipitate is washed with cold water, which is then filtered and dried under vacuum in order to form di-tert phosphate. The di-tert-phosphate (4 g, 19 mmol) is then dissolved in about 100 mL acetone with tetramethylammonium hydroxide added drop-wise until reaching about pH 7, and then the solvent is removed and dried under vacuum to produce tetra-methyl ammonium di-tert-butyl phosphate. Tetra-methyl ammonium di-tert-butyl phosphate (5.11 g, 18 mmol) is then reacted with iodocholoro methane ($CH_2ClI$) (25 g, 142 mmol, 7.88 equivalent) in about 150 ML DME and refluxed for about 2 hours before being filtered to remove the precipitate, removal of the solvent, and then dissolved in EA/H, and then filtered through a silica bed, and the solvent is removed and the product is dried to obtain di-tert-butyl(chloromethyl)phosphate. A TLC is shown to confirm product.

Figure 3:
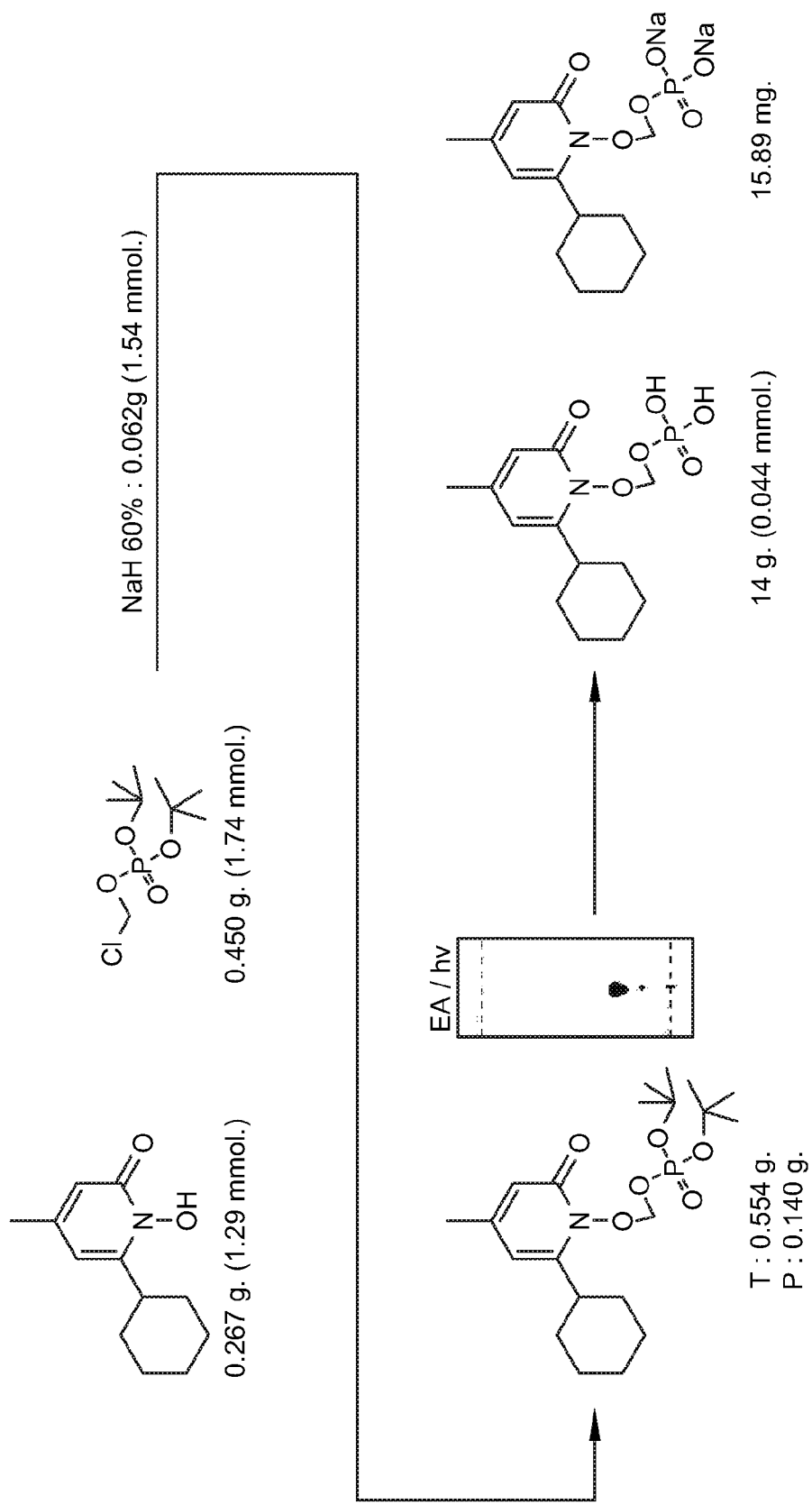
FIG. 3 illustrates a schematic representation of a method of preparing a prodrug of 6-cyclohexyl-1-hydroxy-4-methylpyridin-2(1H)-one (Scheme 3).

In one embodiment, the present invention provides a method of preparing a prodrug of 6-cyclohexyl-1-hydroxy-4-methylpyridin-2(1H)-one (i.e., ((6-cyclohexyl-4-methyl-pyridin-1(2H)-yl)oxy)methyl phosphate disodium salt), which method can include reaction Scheme 3 as shown in FIG. 3. The reaction Scheme 3 reacts ciclopirox with di-tert-butyl(chloromethyl)phosphate to form a ciclopirox-POM that includes a disodium salt. Briefly, ciclopirox (0.257 g, 1.25 mmol) and di-tert-butyl(chloromethyl)phosphate (0.450 g, 1.74 mmol) are dissolved in 5 mL and reacted with 60% NaH (0.62 g, 154. mmol) at 0° C. for 30 minutes and then room temperature for 2 hours before being quenched with water, and then the solvent is removed and process through a separation column with EA/H (1:1) to yield di-tert-butyl (((6-cyclohexyl-4-methylpyridin-1(2H)-yl)oxy)methyl) phosphate, which was confirmed via TLC. The di-tert-butyl (((6-cyclohexyl-4-methylpyridin-1(2H)-yl)oxy)methyl) phosphate was then dissolved in 10 mL THF/$CH_2Cl_2$ (3:1), and incubated at room temperature for 2 hours before the solvent was removed and purified via RPHPLC, and then equamolar $Na_2CO_3$ in water/ACN was added and lyophilized to obtain ((6-cyclohexyl-4-methylpyridin-1(2H)-yl)oxy)methyl dihydrogen phosphate (14 mg, 0.044 mmol) and ((6-cyclohexyl-4-methylpyridin-1(2H)-yl)oxy) methyl phosphate disodium salt (15.89 mg), which is referred to herein as the primary ciclopirox-POM prodrug.

Figure 3A:
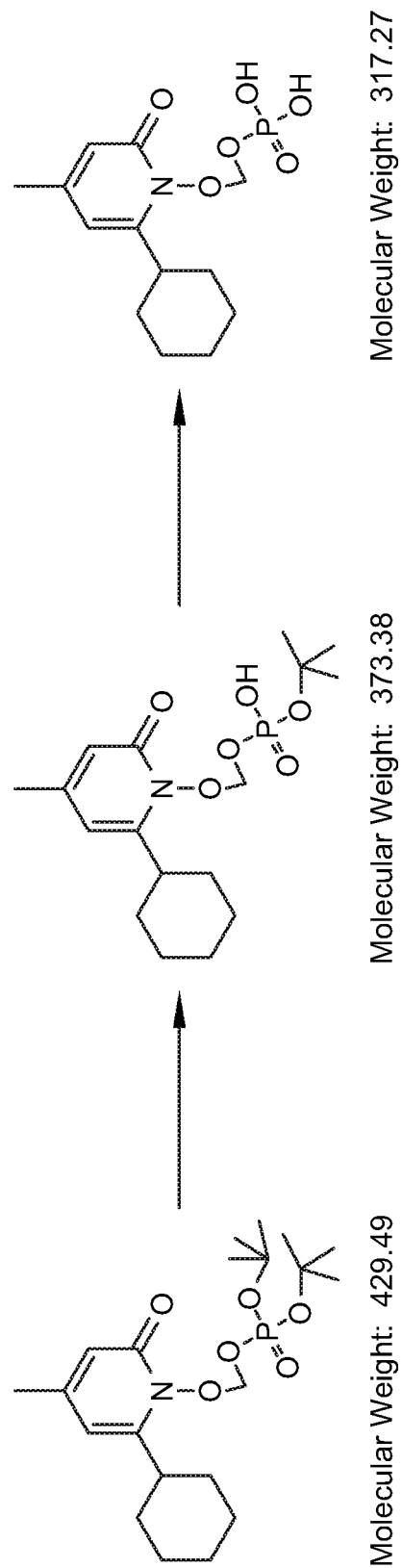
FIG. 3A illustrates a schematic representation of a sub-reaction process identified as Scheme 3A, which can be a sub-process of Scheme 3 of FIG. 3.
Figure 3B:
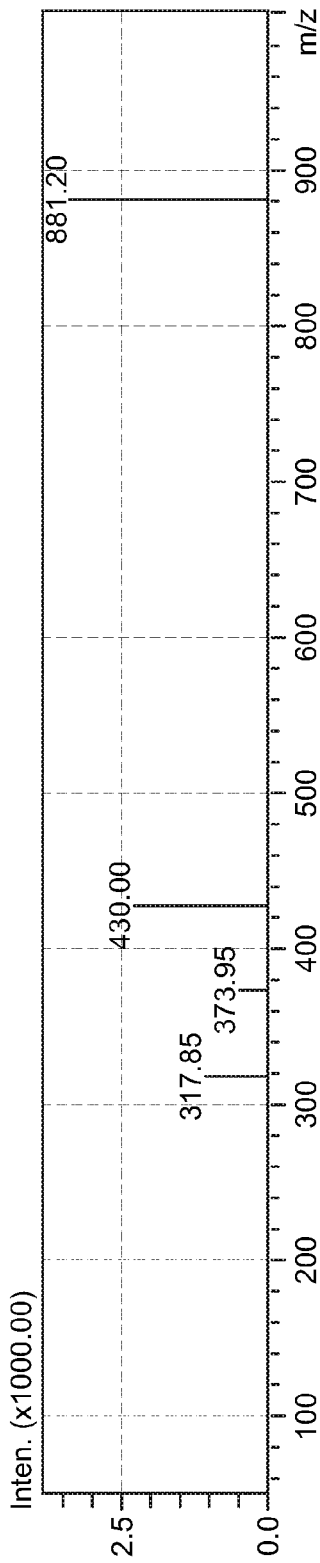
FIG. 3B illustrates a mass spectroscopy chromatograph that shows the reaction products of Scheme 3A of FIG. 3A.

FIG. 3A shows a sub-reaction process identified as Scheme 3A, which can be a sub-process of Scheme 3. Scheme 3A shows the di-tert-butyl ((((6-cyclohexyl-4-methylpyridin-1(2H)-yl)oxy)methyl) phosphate converting to tert-butyl ((((6-cyclohexyl-4-methylpyridin-1(2H)-yl)oxy) methyl) hydrogen phosphate, which converts to ((6-cyclohexyl-4-methylpyridin-1(2H)-yl)oxy)methyldihydrogen phosphate. FIG. 3B shows a mass spectrometry chromatograph that shows the presence of these chemical entities.

Figure 3C:
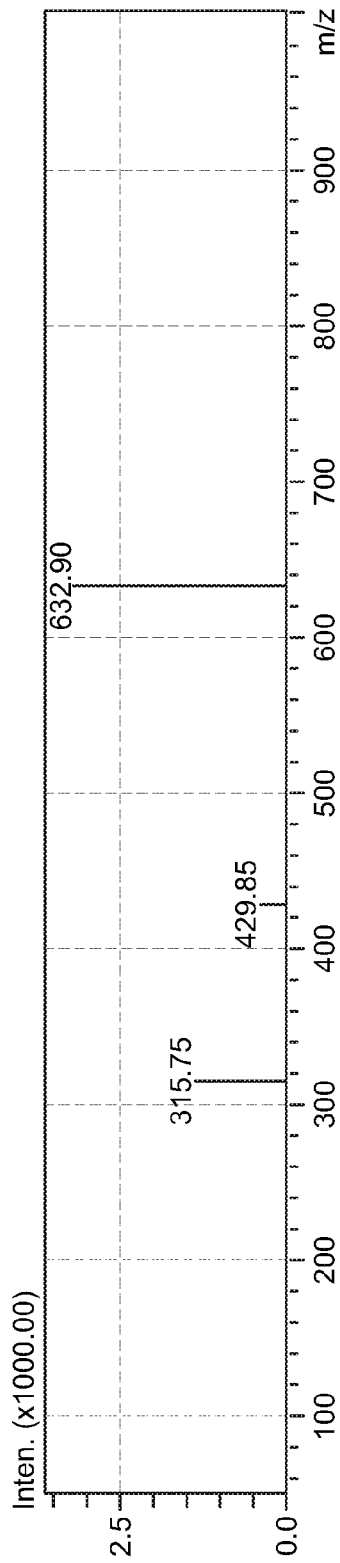
FIG. 3C illustrates a mass spectrometry chromatograph that shows the presence of the free acid form of ((6-cyclohexyl-4-methylpyridin-1(2H)-yl)oxy)methyl dihydrogen phosphate.

The free acid form of the ciclopirox-POM prodrug (i.e., ((6-cyclohexyl-4-methylpyridin-1(2H)-yl)oxy)methyl dihydrogen phosphate) was also purified by RPHPLC as shown in FIG. 3C. The purified product was shown to have a mass spectrometry chromatograph as shown in FIG. 3C.

Figure 3D:
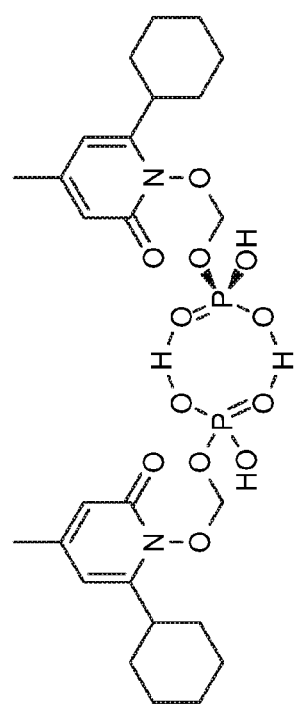
FIG. 3D illustrates a dimer-type form of ciclopirox-POM prodrug.
Figure 3E:
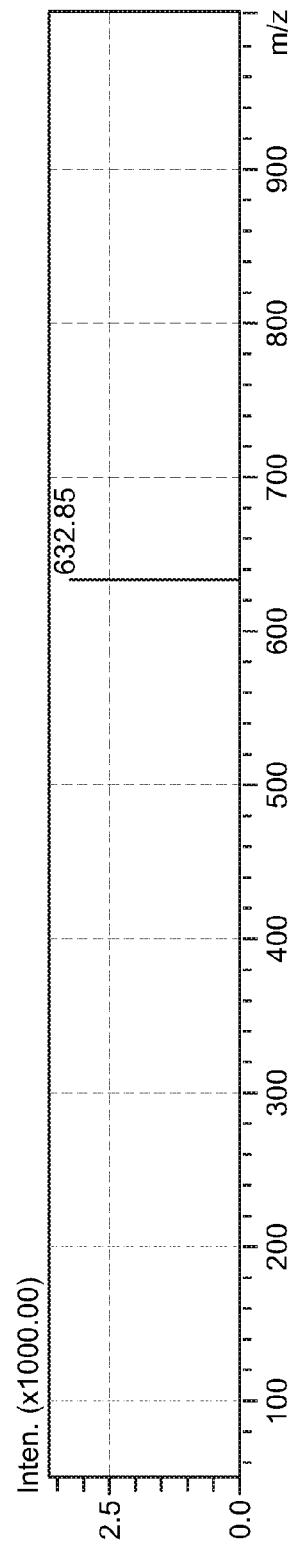
FIG. 3E illustrates a mass spectrometry chromatograph of the dimer-type form of Ciclopirox-POM prodrug of FIG. 3D.

Additionally, another dimer-type form of ciclopirox-POM prodrug has been created as shown in FIG. 3D, which is referred to as the ciclopirox-POM dimer prodrug. The ciclopirox-POM dimer prodrug is confirmed with mass spectrometry chromatograph as shown in FIG. 3E.

Figure 4:
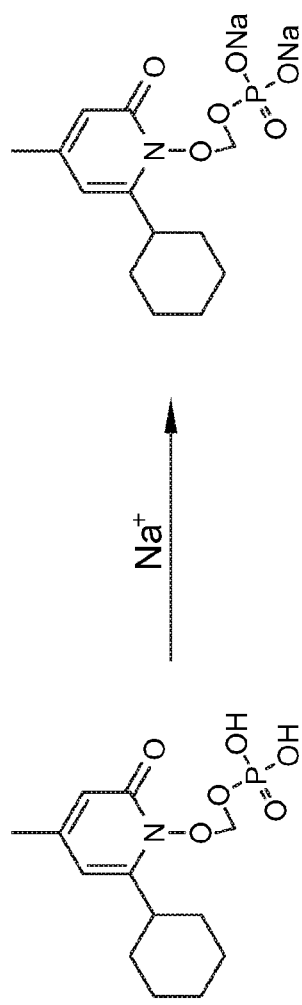
FIG. 4 illustrates a schematic representation of salting ((6-cyclohexyl-4-methylpyridin-1(2H)-yl)oxy)methyl dihydrogen phosphate to obtain ((6-cyclohexyl-4-methylpyridin-1(2H)-yl)oxy)methyl phosphate disodium salt (Scheme 4).
Figure 4A:
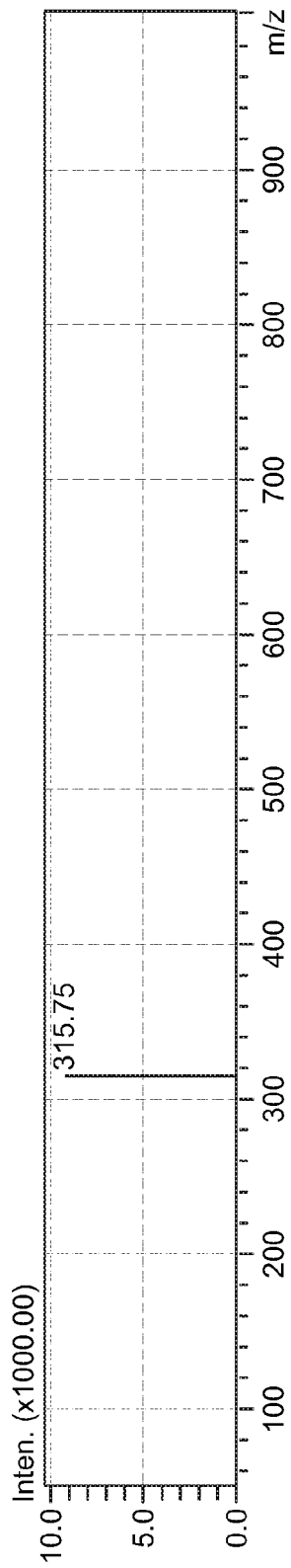
FIG. 4A illustrates a mass spectrometry chromatograph that shows the presence of the ((6-cyclohexyl-4-methylpyridin-1(2H)-yl)oxy)methyl phosphate disodium salt of FIG. 4.

FIG. 4 illustrates Scheme 4 which is the process of salting ((6-cyclohexyl-4-methylpyridin-1(2H)-yl)oxy)methyl dihydrogen phosphate with sodium ions in order to obtain ((6-cyclohexyl-4-methylpyridin-1(2H)-yl)oxy)methyl phosphate disodium salt, which is confirmed with mass spectrometry chromatograph as shown in FIG. 4A.

Figure 5:
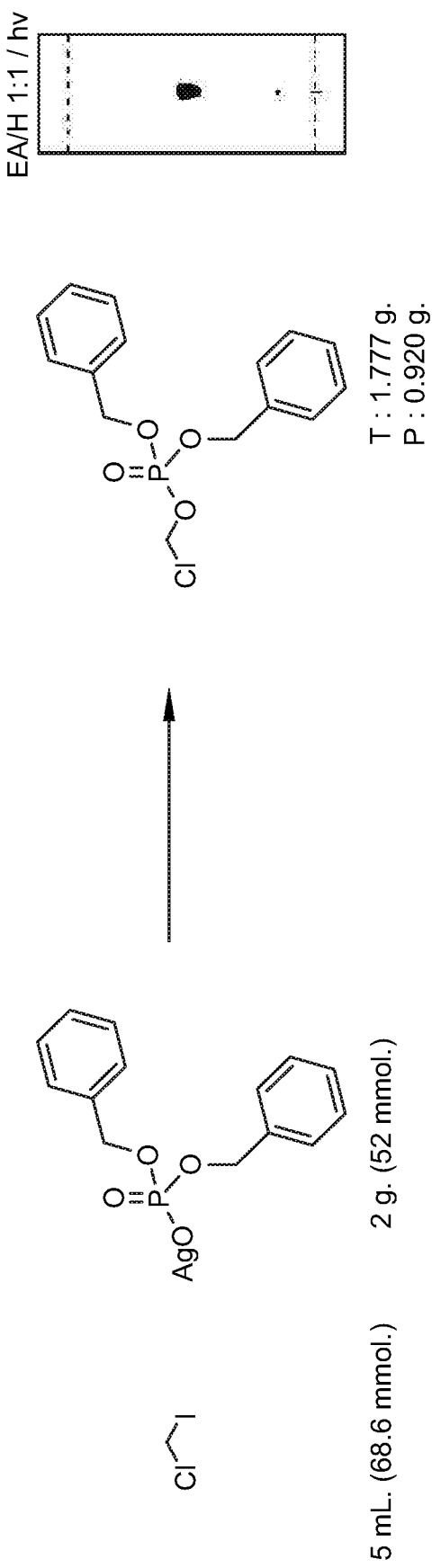
FIG. 5 illustrates a schematic representation of a method of preparing dibenzyl(chloromethyl)phosphate (Scheme 5).

In one embodiment, the present invention can include a method of preparing the POM reagent dibenzyl(chloromethyl)phosphate, as shown in reaction Scheme 5 of FIG. 5. Briefly, $CH_2ClI$ (5 mL; 68.6 mmol) is reacted with silver dibenzyl phosphate (2 g, 52 mmol) in about 25 mL toluene and refluxed for about 1 hour before the solvent is removed and processed through a separation column with 1/1EA/H in order to produce dibenzyl(chloromethyl)phosphate as confirmed via TLC.

Figure 6:
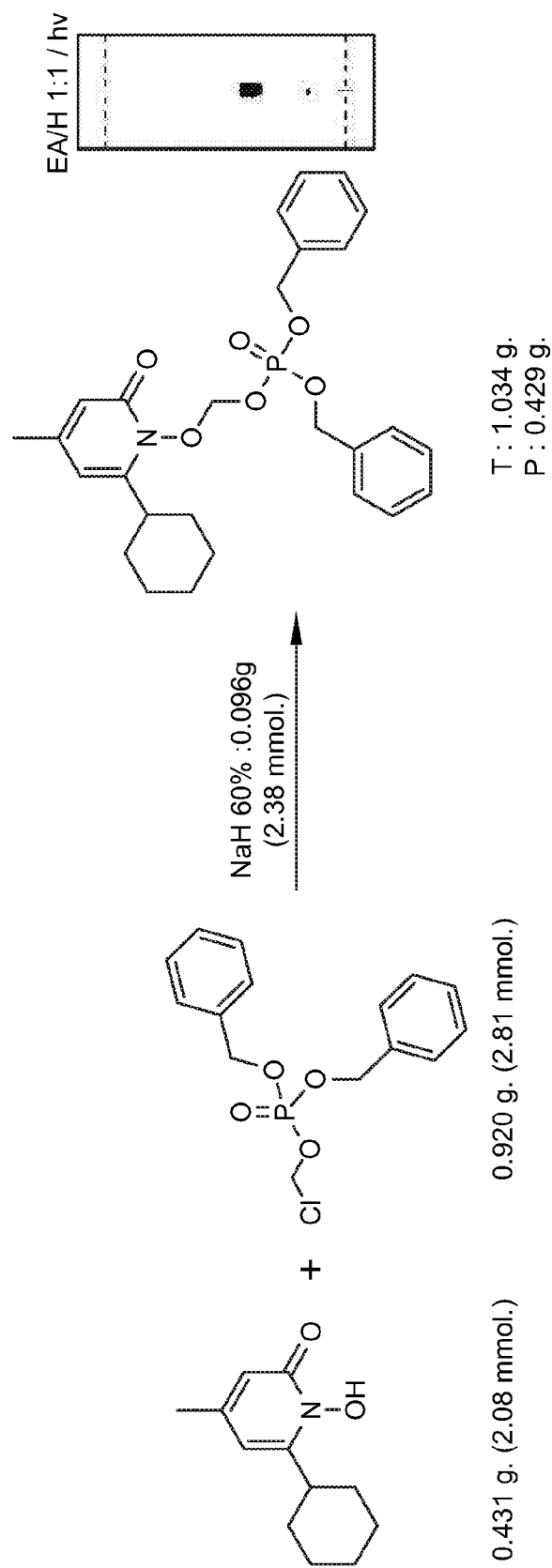
FIG. 6 illustrates a schematic representation of a method of preparing dibenzyl (((6-cyclohexyl-4-methyl-2-oxopyridin-1(2H)-yl)oxy)methyl) phosphate (Scheme 6).

In one embodiment, the present invention provides a method of preparing a prodrug dibenzyl ((((6-cyclohexyl-4-methyl-2-oxopyridin-1(2H)-yl)oxy)methyl) phosphate, which is shown by Scheme 6 of FIG. 6. Briefly, ciclopirox (0.431 g, 2.08 mmol) is dissolved in 10 mL DMF with dibenzyl(chloromethyl)phosphate (0.920 g, 2.81 mmol) along with 60% NaH (0.096 g, 2.38 mmol) and incubated at 0° C. for 30 minutes and then at room temperature for 1 hour before being quenched with water. The solvent is then removed and processed through a separation column with EA/H 1:1 in order to yield dibenzyl ((((6-cyclohexyl-4-methyl-2-oxopyridin-1(2H)-yl)oxy)methyl) phosphate, which is confirmed via the TLC as shown.

Figure 7:
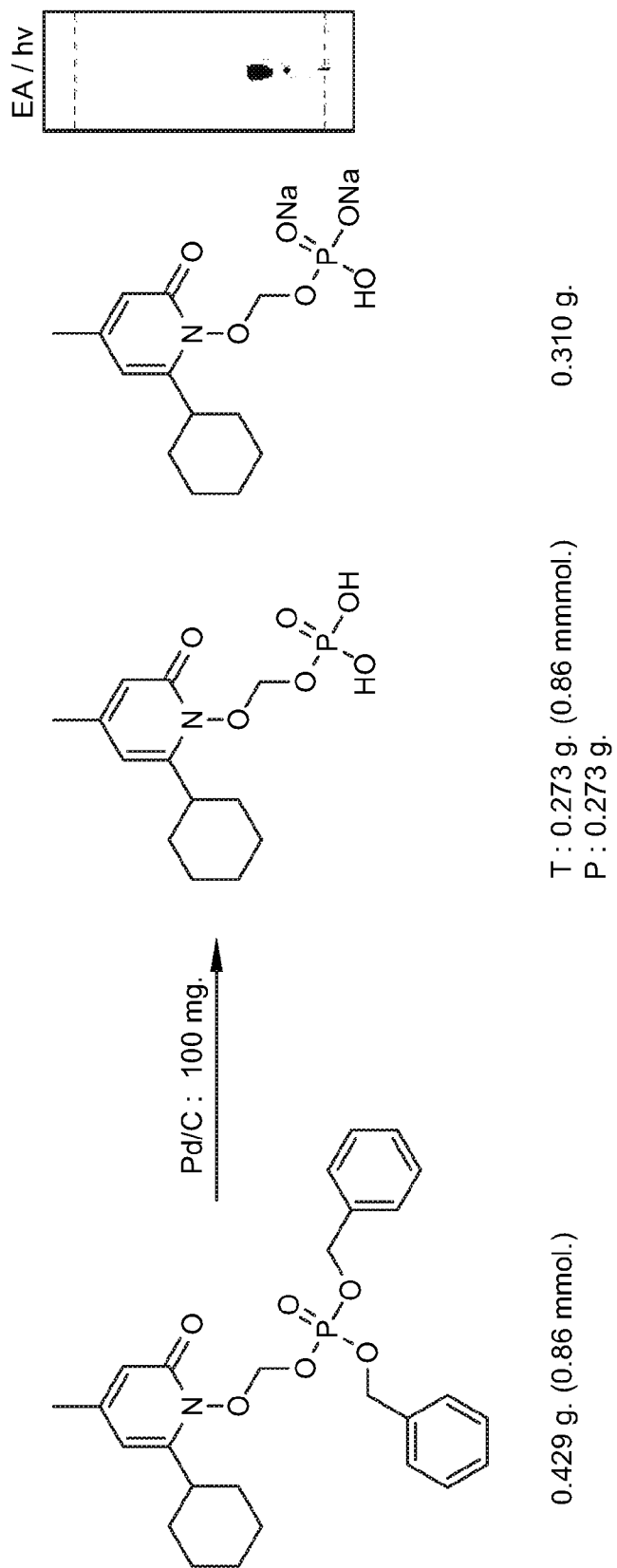
FIG. 7 illustrates a schematic representation of a method of preparing ((6-cyclohexyl-4-methylpyridin-1(2H)-yl)oxy) methyl phosphate di sodium salt (Scheme 7).

In one embodiment, dibenzyl ((((6-cyclohexyl-4-methyl-2-oxopyridin-1(2H)-yl)oxy)methyl) phosphate is converted into ((6-cyclohexyl-4-methylpyridin-1(2H)-yl)oxy)methyl phosphate disodium salt as shown in Scheme 7 of FIG. 7. Briefly, dibenzyl ((((6-cyclohexyl-4-methyl-2-oxopyridin-1 (2H)-yl)oxy)methyl) phosphate is dissolved in 25 mL THF in the presence of 100 mg Pd/C, and under hydrogen ($H_2$) at room temperature for 3 hours before the solvent was removed and the product dissolved in ACN. $Na_2CO_3$ in water is then added and lyophilized. The product is determined to be a minor amount of ((6-cyclohexyl-4-methylpyridin-1(2H)-yl)oxy)methyl dihydrogen phosphate (about 0.273 g, 0.86 mmol) and the major product being ((6-cyclohexyl-4-methylpyridin-1(2H)-yl)oxy)methyl phosphate disodium salt (0.310 g), which was confirmed via TLC as shown.

Figure 8:
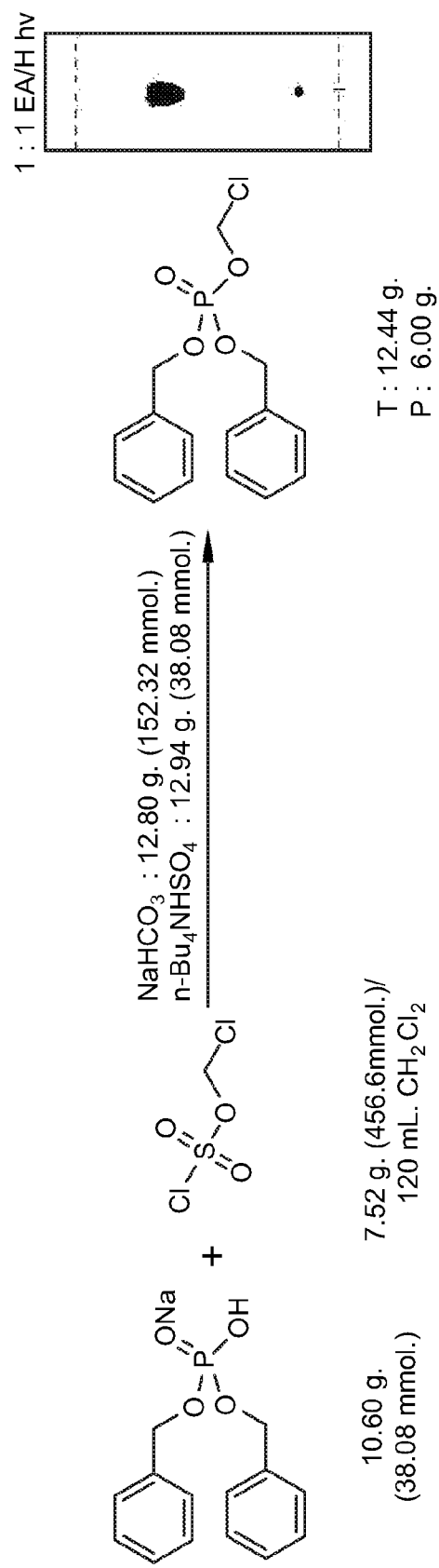
FIG. 8 illustrates a schematic representation of a method of preparing the POM reagent dibenzyl(chloromethyl)phosphate (Scheme 8).

In one embodiment, another method of preparing the POM reagent dibenzyl(chloromethyl)phosphate, as shown in reaction Scheme 8 of FIG. 8. Briefly, dibenzylphosphate (10.6 g; 38.08 mmol) and chloromethyl sulfochloridate (7.52 g, 456.6 mmol/120 mL $CH_2Cl_2$) are dissolved in 320 mL water and 200 mL $CH_2Cl_2$ with $NaHCO_3$ (12.80 g, 152.32 mmol) and n-$Bu_4NHSO_4$ (12.94 g, 38.08 mmol) at 0° C. to room temperature overnight, and then processed through a separation column with ½ EA/H, EA. This reaction yields about 48% of dibenzyl(chloromethyl)phosphate (6 g), which is confirmed with TLC as shown.

In one embodiment, the present invention provides another method of preparing a prodrug dibenzyl ((((6-cyclohexyl-4-methyl-2-oxopyridin-1(2H)-yl)oxy)methyl) phosphate, which is shown by Scheme 6 of FIG. 6. Briefly, Ciclopirox (1 g, 4.82 mmol) is dissolved in 20 mL DMF with dibenzyl(chloromethyl)phosphate (2 g, 6.12 mmol) along with 60% NaH (0.375 g) and incubated at 0° C. for 30 minutes and then at room temperature for 1 hour before being quenched with water. The solvent is then removed, and the product is dissolved in EtOAc, washed with water, solvent is removed, and processed through a separation column with EA/H 1:2, and RPHPLC in order to yield 67% dibenzyl ((((6-cyclohexyl-4-methyl-2-oxopyridin-1(2H)-yl)oxy)methyl) phosphate (1.616 g).

Experimental

The data in the figures and tables indicates that ciclopirox-POM prodrug as described herein can be an improvement for administration to subjects. It was found that ciclopirox was readily bioavailable when given IV as the prodrug, compared to IV administration of ciclopirox olamine to mice, rats and dogs, and thereby the ciclopirox-POM is an improvement in chemical formulation. Following oral administration to mice, however, bioavailability is low, 21% following administration of the olamine salt, and 12% following oral administration of ciclopirox-POM prodrug. Accordingly, ciclopirox is readily bioavailable when given IV as the prodrug. Based on the inability to detect the prodrug in plasma and urine following IV, oral, subcutaneous and intraperitoneal administration, it appears the prodrug is rapidly and completely metabolized to ciclopirox when it reaches the systemic circulation. Thus, ciclopirox-POM prodrug has advantages over ciclopirox olamine, from a physicochemical properties standpoint, and can be formulated into a suitable injectable product. Based on the data, it is reasonable to believe that the ciclopirox-POM prodrug is rapidly converted to ciclopirox.

The ciclopirox-POM prodrug described herein ((((6-cyclohexyl-4-methylpyridin-1(2H)-yl)oxy)methyl phosphate disodium salt, MW 361) was studied and compared with the ciclopirox free base (MW 207) and ciclopirox olamine (MW 268). Equivalent doses of ciclopirox for these three entities were administered such as follows: ciclopirox olamine at 2.0 mg/mL and ciclopirox-POM prodrug at 2.69 mg/mL. The plasma ciclopirox concentrations in (ng/mL) were determined following bolus administration of ciclopirox-POM prodrug at a 10 mg/kg IV bolus in a mouse model. Time points where data collected are shown in Table 1 to be at 5, 15, 30, 60, 90, 120, 180, and 240 minutes along with the data. Additional Samples were collected were collected at 360, 480, 720 and 1440 minutes, however, concentrations fell below BQL of 10 ng/mL, and are not included in PK data analysis. The IV bolus formulation for prodrug was in 25 mM phosphate buffer.

TABLE 1

Plasma Ciclopirox Concentrations (ng/mL): Ciclopirox-POM IV Bolus

| Time (min) | A | B | C | D | E | F | Mean | SD | % CV |
|---|---|---|---|---|---|---|---|---|---|
| 5 | 7280 | 7320 | 6370 | 9700 | 8500 | 8860 | 8005 | 1226.1 | 15.3 |
| 15 | 3310 | 3180 | 1520 | 1370 | 4010 | 3190 | 2763.3 | 1067.3 | 38.6 |
| 30 | 994 | 1200 | 986 | 1030 | 1080 | 452 | 957 | 259.5 | 27.1 |
| 60 | 410 | 259 | 284 | 259 | 409 | 436 | 342.8 | 83.8 | 24.4 |
| 90 | 97.6 | 157 | 74.2 | 79.1 | 162 | 168 | 123 | 43.9 | 35.7 |
| 120 | 58 | 73.7 | 57.9 | 19.3 | 71.7 | 84.8 | 60.9 | 22.8 | 37.4 |
| 180 | 18.1 | 23 | 19.5 | 34.8 | 19.7 | 37.7 | 25.5 | 8.6 | 33.6 |
| 240 | 13 | 10 | 15 | 12 | 10 | 8 | 11.1 | 2.6 | 23.6 |

The plasma ciclopirox concentrations in (ng/mL) were determined following bolus administration of ciclopirox olamine at a 10 mg/kg IV bolus in a mouse model. Time points where data collected are shown in Table 1 to be at 5, 15, 30, 60, 90, 120, 180, and 240 minutes along with the data. The IV bolus formulation for ciclopirox olamine was in 0.05 M Captisol® and 25 mM phosphate buffer, and the corresponding data is shown below in Table 2. Additional Samples were collected were collected at 360, 480, 720 and 1440 minutes, however, concentrations fell below BQL of 10 ng/mL, and are not included in PK data analysis

TABLE 2

Plasma Ciclopirox Concentrations (ng/mL): Ciclopirox Olamine IV Bolus

| Time (min) | A | B | C | D | E | F | Mean | SD | % CV |
|---|---|---|---|---|---|---|---|---|---|
| 5 | 6090 | 3490 | 5830 | 4480 | 3930 | 5430 | 4875 | 1064.3 | 21.8 |
| 15 | 543 | 591 | 1410 | 1100 | 739 | 968 | 891.8 | 332.6 | 37.3 |
| 30 | 545 | 371 | 166 | 339 | 336 | 364 | 353.5 | 120.6 | 34.1 |
| 60 | 171 | 127 | 124 | 144 | 110 | 124 | 133.3 | 21.4 | 16.1 |
| 90 | 45.2 | 63.4 | 58.8 | 42.9 | 58 | 84 | 58.7 | 14.8 | 25.2 |
| 120 | 46.1 | 41.2 | 46.9 | 39.2 | 42.4 | OL | 43.2 | 17.6 | 48.9 |
| 180 | 14 | 18.9 | 18.1 | 28.7 | 47.2 | 24.5 | 25.2 | 11.9 | 47.3 |
| 240 | 12 | 12 | 21 | 16 | OL | 19 | 15.9 | 4.2 | 26.6 |

The plasma ciclopirox (i.e., CPX) concentrations in (ng/mL) were determined following bolus administration of ciclopirox-POM prodrug at a 30 mg/kg orally in a mouse model. Time points where data collected are shown in Table 3 to be at 5, 15, 30, 60, 90, 120, 180, and 240 minutes along with the data. Additional Samples were collected were collected at 360, 480, 720 and 1440 minutes, however, concentrations fell below BQL of 10 ng/mL, and are not included in PK data analysis. The oral formulation is a composition having Orasweet SF along with the ciclopirox-PIM prodrug.

TABLE 3

Plasma Ciclopirox Concentrations (ng/mL): Ciclopirox-POM Oral Dose

| Time (min) | A | B | C | D | E | F | Mean | SD | % CV |
|---|---|---|---|---|---|---|---|---|---|
| 0 | 0 | 0 | 0 | 0 | 0 | 0 | 0 | ND | ND |
| 15 | 388 | 646 | 857 | 245 | 479 | 507 | 520.3 | 211.8 | 40.7 |
| 30 | 302 | 252 | 264 | 317 | 207 | 342 | 280.7 | 49.1 | 17.5 |
| 60 | 129 | 404 | 154 | 229 | 171 | 207 | 215.7 | 99 | 45.9 |
| 90 | 91 | 66.8 | 146 | 137 | 120 | 80.3 | 106.9 | 32.2 | 30.1 |
| 120 | 72.5 | 60.6 | 64.6 | 81.4 | 83.6 | OL | 72.5 | 39.6 | 54.6 |
| 180 | 36.8 | 45.1 | 59.1 | 66.4 | 44.9 | 44 | 49.4 | 11 | 22.4 |
| 240 | 9.51 | OL | 19 | 14.7 | 38.1 | 19 | 20.1 | 10.8 | 53.9 |

The plasma ciclopirox concentrations in (ng/mL) were determined following bolus administration of ciclopirox olamine at a 30 mg/kg oral dose in a mouse model. Time points where data collected are shown in Table 1 to be at 5, 15, 30, 60, 90, 120, 180, and 240 minutes along with the data. The oral formulation for ciclopirox olamine was a suspension of Orasweet SF, and the corresponding data is shown below in Table 4. Additional Samples were collected were collected at 360, 480, 720 and 1440 minutes, however, concentrations fell below BQL of 10 ng/mL, and are not included in PK data analysis

TABLE 4

Plasma Ciclopirox Concentrations (ng/mL): Ciclopirox Olamine Oral Dose

| Time (min) | A | B | C | D | E | F | Mean | SD | % CV |
|---|---|---|---|---|---|---|---|---|---|
| 0 | 0 | 0 | 0 | 0 | 0 | 0 | 0 | ND | ND |
| 15 | 478 | OL | 625 | 445 | 565 | 626 | 547.8 | 83.4 | 15.2 |
| 30 | 427 | 376 | 430 | 432 | 388 | 641 | 449 | 97 | 21.6 |
| 60 | 379 | 319 | 501 | 211 | 246 | 196 | 308.7 | 116.8 | 37.8 |
| 90 | 124 | 297 | 259 | 348 | 337 | 198 | 260.5 | 86.5 | 33.2 |
| 120 | OL | 101 | 146 | 85.4 | 204 | 218 | 150.9 | 59.4 | 39.4 |
| 180 | 78.2 | 83.4 | 76.4 | 107 | 66.5 | 69.2 | 80.1 | 14.5 | 18.1 |
| 240 | 72.3 | 93.1 | 92.5 | 48.9 | 67.8 | 73.6 | 74.7 | 16.6 | 22.2 |

Additionally, mouse intravenous dose pharmacokinetics were determined. Briefly, the pharmacokinetics were determined for mouse hepatic blood flow at 90 mL/min/kg, an ciclopirox would be considered a medium clearance drug with extraction ration of 0.6 The IV bolus pharmacokinetics are shown in Table 5 below.

TABLE 5

Ciclopirox Pharmacokinetics (10 mg/kg IV Bolus)

| PK Parameter | CPX Prodrug mg/kg | CPX Olamine 10 mg/kg |
|---|---|---|
| Alpha rate constant (min−1) | 0.07043 | 0.08802 |
| Alpha Half-life (min) | 9.84 | 7.87 |
| Beta rate constant (min−1) | 0.01929 | 0.01208 |
| Beta Half-life (min) | 35.92 | 57.35 |
| AUC (ng/mL/kg) | 160330 | 140313 |

TABLE 5-continued

Ciclopirox Pharmacokinetics (10 mg/kg IV Bolus)

| PK Parameter | CPX Prodrug mg/kg | CPX Olamine 10 mg/kg |
|---|---|---|
| CL (mL/min/kg) | 48.275* | 55.162* |
| Vdbeta (mL/kg) | 2502 | 4565.2 |

Additionally, mouse oral dose pharmacokinetics were determined. Briefly, the pharmacokinetics were determined for mouse hepatic blood flow at 90 mL/min/kg, an ciclopirox would be considered a medium clearance drug with extraction ration of 0.6 The oral pharmacokinetics are shown in Table 6 below.

TABLE 6

Ciclopirox Pharmacokinetics (30 mg/kg Oral)

| PK Parameter | CPX Prodrug 30 mg/kg | CPX Olamine 30 mg/kg |
|---|---|---|
| Cmax (ng/mL) | 520.3 | 547.8 |
| Tmax (min) | 15 | 15 |
| Beta rate constant (min−1) | 0.01316 | 0.00916 |
| Beta Half-life (min) | 52.76 | 75.67 |
| AUC (ng/mL/kg) | 32157.91 | 57389.8 |
| CL/F (mL/min/kg) | 722.06 | 404.602 |

The IV bolus and oral administration of ciclopirox-POM prodrug and ciclopirox olamine were also studied with regard to bioavailability of ciclopirox. The data is shown in Table 7. The IV bolus and oral administrations are described above.

TABLE 7

Bioavailability of Ciclopirox (IV Bolus v. Oral)

| PK Parameter | IV Administration | Oral Administration |
|---|---|---|
| CPX AUC (ng/mL/kg) | | |
| Prodrug | 160330.3 | 32157.91 |
| Olamine Salt | 140312.6 | 57389.8 |
| Foral | | |
| Prodrug | | 0.066858 |
| Olamine Salt | | 0.136338 |
| CPX Bioavailability Following Prodrug Administration | 1.142665 | 0.560342 |

The data in the foregoing tables indicates that ciclopirox-POM prodrug as described herein can be an improvement for administration to subjects. Based on intravenous pharmacokinetics following administration of ciclopirox olamine, ciclopirox is considered a medium clearance drug based on intravenous clearance compared to hepatic blood flow in the mouse. It was found that ciclopirox was completely bioavailable when given IV as the prodrug, compared to IV administration of ciclopirox olamine, and thereby the ciclopirox-POM is an improvement in chemical formulation. The data shows that ciclopirox was 50% bioavailable, when given as orally as the prodrug, compared to CPX Olamine administered as an oral suspension, which shows an improvement in ciclopirox-POM prodrug. Accordingly, ciclopirox is readily bioavailable when given IV as the prodrug. Based on the inability to detect the prodrug in plasma following IV and oral administration, it appears the prodrug is rapidly metabolized to ciclopirox when it reaches the systemic circulation. Thus, ciclopirox-POM prodrug has advantages over ciclopirox olamine, from a physicochemical properties standpoint, and can be formulated into a suitable IV product. Based on the data, it is reasonable to believe that the ciclopirox-POM prodrug is rapidly converted back to ciclopirox.

The term "alkyl" or "aliphatic" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to about 12 carbon atoms. The term "lower alkyl" intends an alkyl group of 1 to 6 carbon atoms. Substituents identified as "$C_1$-$C_6$ alkyl" or "lower alkyl" contains 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The terms "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein contain 1 to 3 carbon atoms, and such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 5 to 20 carbon atoms, and aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethyinaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, and fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrocarbyl" refers to univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, heteroatom-containing alkenyl, and heteroatom-containing aryl."

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited or in the incorporated references herein are incorporated herein by specific reference in their entirety.

The invention claimed is:

1. A method of forming an active compound in a subject, the method comprising:
    providing a composition having a prodrug compound represented by a structure of Formula 1 or stereoisomer thereof or pharmaceutically acceptable salt thereof; and
    administering the composition to a subject such that the prodrug compound has a phosphoryloxyalkyl prodrug moiety removed therefrom to form the active compound and a phosphoryloxyalkyl compound in the subject,

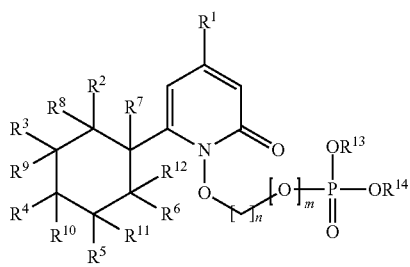

Formula 1 wherein:
    $R^1$ is a short aliphatic;
    $R^2$-$R^{12}$ each include hydrogen;
    $R^{13}$-$R^{14}$ each independently include one or more of a positive ion, sodium ion, hydrogen, straight aliphatics, branched aliphatics, cyclic aliphatics, substituted aliphatics, unsubstituted aliphatics, saturated aliphatics, aromatics or substituted aromatics, hetero;
    n is 1; and
    m is 1.

2. The method of claim 1, the prodrug compound is represented by a structure of Formula 2 or stereoisomer thereof or pharmaceutically acceptable salt thereof

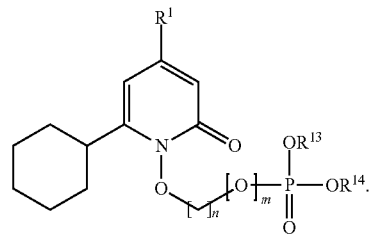

Formula 2

3. The method of claim 1, the prodrug compound is represented by a structure of Formula 3 or stereoisomer thereof or pharmaceutically acceptable salt thereof

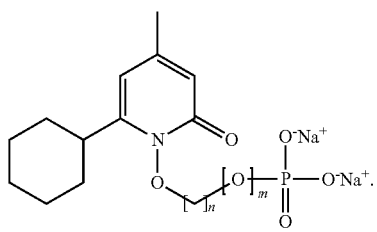

Formula 3

4. The method of claim 1, the prodrug compound is represented by a structure of Formula 4 or stereoisomer thereof or pharmaceutically acceptable salt thereof

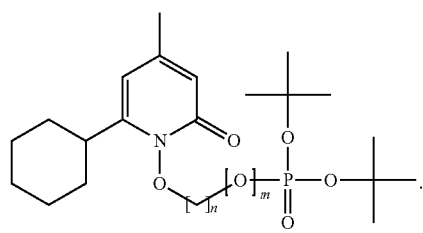

Formula 4

5. The method of claim 1, the prodrug compound is represented by a structure of Formula 5 or stereoisomer thereof or pharmaceutically acceptable salt thereof

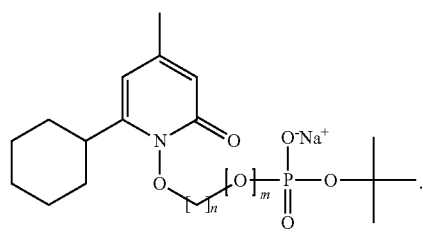

Formula 5

6. The method of claim 1, the prodrug compound is represented by a structure of Formula 6 or stereoisomer thereof or pharmaceutically acceptable salt thereof Formula 6

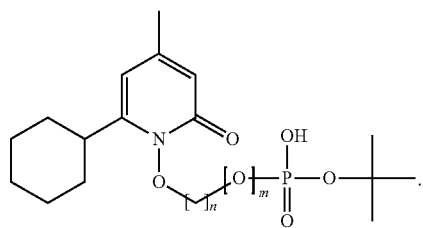

7. The method of claim 1, the prodrug compound is represented by a structure of Formula 7 or stereoisomer thereof or pharmaceutically acceptable salt thereof Formula 7

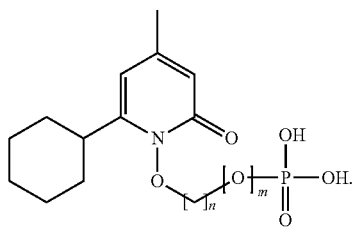

8. The method of claim 1, the prodrug compound is represented by a structure of Formula 8 or stereoisomer thereof or pharmaceutically acceptable salt thereof Formula 8

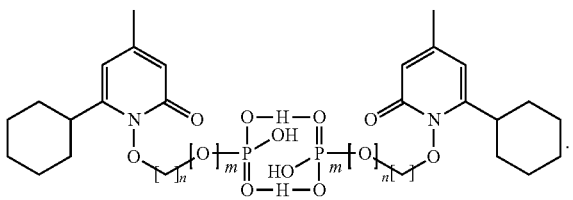

9. The method of claim 1, the prodrug compound is represented by a structure of Formula 9 or stereoisomer thereof or pharmaceutically acceptable salt thereof Formula 9

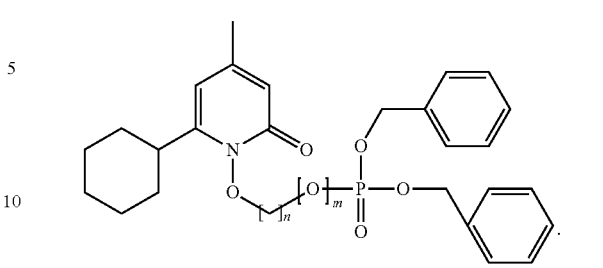

10. The method of claim 1, the prodrug compound is represented by a structure of Formula 10 or stereoisomer thereof or pharmaceutically acceptable salt thereof Formula 10

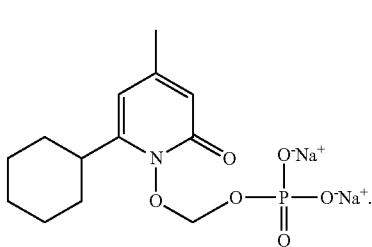

11. The method of claim 1, wherein the pharmaceutical composition comprises the compound and a pharmaceutically acceptable carrier.

12. The method of claim 1, wherein the composition is administered in an amount to provide 6-cyclohexyl-1-hydroxy-4-methylpyridin-2(1H)-one as the active compound.

13. The method of claim 1, wherein the phosphoryloxyalkyl prodrug moiety is enzymatically cleaved from the prodrug compound so as to form the compound.

14. The method of claim 1, wherein the compound is formed in an amount sufficient for disrupting DNA repair in a cell in the subject.

15. The method of claim 1, wherein the compound is formed in an amount sufficient for disrupting cell division in the subject.

16. The method of claim 1, wherein the compound is formed in an amount sufficient for disrupting intranuclear transport in a cell in the subject.

\* \* \* \* \*